(12) United States Patent
Alsters et al.

(10) Patent No.: US 6,355,842 B1
(45) Date of Patent: Mar. 12, 2002

(54) PROCESS FOR THE OXIDATION OF SUBSTRATES CONTAINING METHYL, METHYLENE OR METHINE GROUPS

(75) Inventors: Paul Alsters, KZ Maastricht; Sabine Bouttemy, EL Geleen, both of (NL)

(73) Assignee: DSM Fine Chemicals Austria Nfg GmbH & CoKG, Linz (AT)

( * ) Notice: Subject to any disclaimer, the term of this patent is extended or adjusted under 35 U.S.C. 154(b) by 0 days.

(21) Appl. No.: 09/448,281

(22) Filed: Nov. 24, 1999

(30) Foreign Application Priority Data

Nov. 25, 1998 (AT) .............................................. 1974/98
Nov. 25, 1998 (AT) .............................................. 1975/98
Jun. 29, 1999 (AT) .............................................. 1127/99

(51) Int. Cl.$^7$ ...................... C07C 45/00; C07D 223/00; B01J 31/00
(52) U.S. Cl. ........................ 568/312; 568/325; 540/484; 502/167; 502/152
(58) Field of Search ................................ 502/167, 152; 540/484; 568/312, 325

(56) References Cited

U.S. PATENT DOCUMENTS

| 3,642,775 A | 2/1972 | Schindler | 260/239 |
| 3,716,640 A | 2/1973 | Schindler | 424/244 |
| 5,030,739 A | 7/1991 | Foricher et al. | 552/542 |

FOREIGN PATENT DOCUMENTS

| EP | 198351 | * 10/1986 |
| EP | 824962 | * 10/1986 |
| EP | 878458 | * 11/1998 |
| WO | 9728897 | * 8/1997 |

* cited by examiner

Primary Examiner—Richard L. Raymond
Assistant Examiner—Sudhaker B. Patel
(74) Attorney, Agent, or Firm—Wenderoth, Lind & Ponack, LLP

(57) ABSTRACT

Process for the oxidation of substrates containing methyl, methylene or methine groups by cooxidation with an aldehyde as cosubstrate in the presence of a catalyst system consisting of an imide compound and a metal cocatalyst.

10 Claims, No Drawings

PROCESS FOR THE OXIDATION OF SUBSTRATES CONTAINING METHYL, METHYLENE OR METHINE GROUPS

The oxidation reaction is one of the most fundamental reactions in organic chemistry and the literature therefore describes many variants. Recently, N-hydroxyphthalimide (NHPI) was disclosed as a suitable catalyst for oxidation reactions under mild conditions. According to EP-A1-0 824 962, NHPI or other imide compounds is or are combined with a metal cocatalyst and used for the oxidation of a multiplicity of organic substances. The oxidation of isoprenoids which have an allylic group to give hydroperoxides, which are then converted into the corresponding alcohols, aldehydes or ketone, is described in EP 0 198 351. N-hydroxydicarboximides are used as a catalyst. As a variant, Einhorn in Chem. Commun. 1997, pages 447–448, describes the use of NHPI in combination with acetaldehyde as catalysts for the oxidation of organic substrates, in particular of hydrocarbons.

There is nevertheless a lack of oxidation systems with oxygen as oxidizing agent which guarantee selective oxidation under conditions which are as mild as possible, since the variants known to date have a low selectivity and low reaction rate as disadvantages in the case of many compounds.

Unexpectedly, it has now been found that the use of a combination consisting of imide compound and metal cocatalyst in the presence of an aldehyde as cosubstrate permits the oxidation of a multiplicity of organic substrates under extremely mild conditions with high selectivity and high reaction rate.

The present invention accordingly relates to a process for the oxidation of substrates containing methyl ($CH_3$), methylene ($CH_2$) or methine (CH) groups by means of oxygen oxidation with the use of a catalyst system comprising an imide compound and a metal cocatalyst, wherein the substrates are oxidized together with an aromatic or aliphatic aldehyde having 2–20C. atoms in the presence of a catalyst system consisting of a) an imide compound of the formula

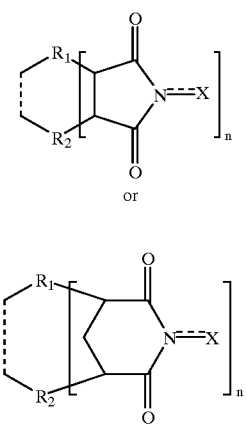

I or

II in which $R_1$ and $R_2$ may denote H, OH, halogen, a $C_1$–$C_{20}$-alkyl, alkenyl or alkoxy group, an aryl group, a $C_1$–$C_6$-acyl group, a carboxyl or a $C_1$–$C_{10}$-alkoxycarbonyl group, or $R_1$ and $R_2$ together form a double bond in the formula I or form an aromatic or nonaromatic ring system in the formula I or II, X may denote O or OH and n may be an integer from 1 to 3, and b) a cocatalyst containing one or more elements from the group consisting of the transition metals and of the 2A and 3A elements of the Periodic Table, in an organic solvent to give the corresponding oxo compounds.

Substrates containing methyl, methylene or methine groups serve as a starting compound for the process according to the invention. Suitable substrates are described, for example, in EP-A1-0 824 962 and include aliphatic, alicyclic or aromatic hydrocarbons which may be saturated or mono- or polyunsaturated, heterocycles, alcohols, esters, aldehydes, ketones and amines. The substrates may have one or more substituents, such as, for example, halogens (F, Cl, Br, I), $C_1$–$C_6$-alkyl groups, oxo groups, hydroxyl groups, $C_1$–$C_6$-alkoxy groups, hydroxy-$C_1$–$C_4$-alkyl groups, carboxyl groups, $C_1$–$C_6$-alkoxycarbonyl groups, $C_1$–$C_6$-acyl groups, amino groups, substituted amino groups, cyano groups, nitro groups and the like.

Compounds which contain an aryl-$CH_2$ group, such as, for example, indanes, 1,2-diphenylethane and dibenz[b,f] azepines, e.g. 10,11-dihydro-5H-dibenz[b,f]-azepinecarboxamide, or compounds which contain methylene groups activated by carboxyl or carbonyl groups are preferably oxidized using the process according to the invention.

The process according to the invention uses a catalyst system consisting of 2 components, in combination with an aldehyde as cosubstrate. A suitable catalyst system is described, for example, in EP 0 824 962. Suitable imide compounds of the formula I for component a) are accordingly compounds of the formula I in which $R_1$ and $R_2$ may thus be identical or different and denote hydrogen, hydroxyl, halogen, such as I, Cl, F or Br, $C_1$–$C_{10}$-alkyl or alkoxy.

$C_1$–$C_{20}$-Alkyl are to be understood as meaning straight-chain, branched or cyclic alkyl radicals, such as, for example, methyl, ethyl, propyl, isopropyl, butyl, isobutyl, sec-butyl, tert-butyl, pentyl, cyclopentyl, hexyl, cyclohexyl, heptyl, octyl, cyclooctyl, decyl, dodecyl, etc. $C_1$–$C_{15}$-Alkyl groups are preferred, particularly preferably $C_1$- to $C_{12}$-alkyl groups. $C_1$–$C_{20}$-Alkenyl are to be understood as meaning straight-chain or branched alkenyl radicals. Examples of these are propenyl, hexenyl, octenyl, decenyl, dodecenyl, etc. $C_4$- to $C_{18}$-Alkenyl groups are preferred, particularly preferably $C_6$- to $C_{12}$-alkenyl groups. $C_1$–$C_{20}$-Alkoxy groups are to be understood as meaning, for example, methoxy, ethoxy, propoxy, isopropoxy, butoxy, isobutoxy, tert-butoxy, pentyloxy and hexyloxy groups, etc. $C_1$–$C_6$-Alkoxy groups are once again preferred, particularly preferably $C_1$–$C_4$-alkoxy groups. $R_1$ and $R_2$ may furthermore denote an aryl group, such as, for example, a phenyl group or a naphthyl group, a $C_1$–$C_6$-acyl group, such as, for example, formyl, acetyl, propionyl, butyryl, isobutyryl, valeryl, isovaleryl, pivaloyl, etc. $R_1$ and $R_2$ may also be a carboxyl group or an alkoxycarbonyl group. Suitable alkoxycarbonyl groups are those which contain 1–10 C atoms in the alkoxy moiety. Examples of these are methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, etc. Preferred groups are those which contain 1–6 C atoms, particularly preferably 1–4 C atoms, in the alkoxy moiety.

However, $R_1$ and $R_2$ may also together form a double bond in the formula I or an aromatic or nonaromatic ring system in the formula I or II, which ring system consists of one or more fused rings. Aromatic or nonaromatic ring systems having 5–12 C atoms, preferably having 6–10 C atoms, are preferred. The rings may also be heterocycles.

Examples of these are cyclohexane or other cycloalkane rings which may optionally be substituted, and cyclohexene or other cycloalkene rings which once again may optionally be substituted, nonaromatic, bridged rings, a benzene ring, a naphthalene ring and other optionally substituted aromatic rings. Compounds of the formula I may have either a saturated or an unsaturated N-containing 6-membered ring. X in the formula I or formula II denotes O or OH. Depending on the meaning of X, the bond between N and X denotes either a double bond or a single bond. n denotes an integer from 1 to 3, preferably 1 or 2.

Preferred imide compounds are N-hydroxysuccinimide, N-hydroxymaleimide, N-hydroxyhexahydrophthalimide, N,N'-dihydrocyclohexanetetracarboximide, N-hydroxyphthalimide, N-hydroxytetrabromophthalimide, N-hydroxytetrachlorophthalimide, N-hydroxytrimellitimide, N,N'-dihydroxynaphthalenetetracarboximide, N-hydroxy(dodecenyl)succinimide, N-hydroxy(octenyl)-succinimide, N-hydroxynaphthalimide, etc.

A cocatalyst is used as component b). The cocatalysts described in EP 0 824 962 are suitable for the catalyst system according to the invention. The cocatalyst accordingly contains one or more elements from the group consisting of 2A elements of the Periodic Table, such as Mg, Ca, Sr, Ba, or of the 3A elements, such as B or Al, or of the transition elements. Suitable transition elements are, for example, elements of the Periodic Table from group 3B, such as Sc, Y, La, Ce, Sm or lanthanoids, Ac or other actinoids, from group 4B (Ti, Zr, Hf), group 5B (V, Nb, Ta), group 6B (Cr, Mo, W), group 7B (Mn, Tc, Re), group 8 (Fe, Ru, Os, Co, Rh, Ir, Ni, Pd, Pt), group 1B (Cu, Ag, Au) and from group 2B (e.g. Zn, Cd).

Preferably used cocatalysts are those which contain Ti, Zr or other group 4B elements, V or other 5B elements, Cr, Mo, W or other group 6B elements, Mn, Tc, Re or other group 7B elements, Fe, Ru, Co, Rh, Ni or other group 8 elements or Cu or other group 1B elements.

Combinations of elements of group 6B and/or 8 or 1B are particularly preferred. The cocatalysts may be used as a metal hydroxide, metal oxide, as an organic salt, as an inorganic salt, etc. Hydroxides are, for example, $Mn(OH)_2$, $MnO(OH)$, $Fe(OH)_2$ and $Fe(OH)_3$. Suitable oxides are, for example, $Sm_2O_3$, $TiO_2$, $ZrO_2$, $V_2O_3$, $V_2O_5$, $CrO$, $Cr_2O_3$, $MoO_3$, $MnO$, $Mn_3O_4$, $Mn_2O_3$, $MnO_2$, $Mn_2O_7$, $FeO$, $Fe_2O_3$, $Fe_3O_4$, $RuO_2$, $RuO_4$, $CoO$, $CoO_2$, $Co_2O_3$, $Cu_2O_3$, etc. Organic salts are, for example, formates, acetates, propionates, acetylacetonates, naphthenates, stearates and other salts of Co, Mn, Ce, Ti, Zr, V, Cr, Mo, Fe, Ru, Ni, Pd, Cu and Zn with $C_2$–$C_{20}$ fatty acids. Inorganic salts include, for example, nitrates, sulfates, phosphates, carbonates and halides of Co, Fe, Mn, Ni, Cu, etc. The cocatalyst may also be used in the form of a complex, as described, for example, in EP-A1-0 824 962. The cocatalyst is preferably used in the form of an organic salt, e.g. acetate, acetylacetonate, etc., and in the form of an inorganic salt, e.g. nitrate, etc.

A particularly preferably used cocatalyst is Ni or Cu, for example as acetate or nitrate. In a further particularly preferred embodiment, Ni or Cu is added in combination with Cr as component b). The combination of Ni or Cu with Cr and traces of Co as cocatalyst is very particularly preferably used.

The components a) and b) of the system according to the invention may form both a homogeneous and heterogeneous system. The components a) and b) can, if desired, be applied in the solid form to a support. Suitable supports are, for example, silica, zeolite, active carbon, etc. or other porous supports.

An aldehyde is used as a cosubstrate in the process according to the invention. Suitable aldehydes are both saturated and unsaturated aliphatic as well as aromatic aldehydes or dialdehydes having 2 to 20 C atoms. Examples of these are acetaldehyde, propionaldehyde, butyraldehyde, valeraldehyde, capronaldehyde, benzaldehyde, naphthaldehyde, o-phthalaldehyde, etc.

Acetaldehyde or benzaldehyde is preferably used as a cosubstrate.

The amounts of the individual components used are for component a):
  0.001 to 0.7 mol, particularly preferably 0.01 to 0.5 mol, per mol of substrate
for component b):
  0.0001 mol to 0.5 mol, preferably 0.0001 to 0.3 mol, particularly preferably from 0.001 to 0.2 mol, per mol of substrate and
for the cosubstrate:
  0.1 to 3 mol, preferably 0.2 to 2.5 mol, per mol of substrate.

The molar ratio of cocatalyst to imide compound is from 0.001 to 1 mol, preferably from 0.001 to 0.8 mol, particularly preferably from 0.002 to 0.2 mol, per mol of imide compound.

If a combination of Ni or Cu and Cr is used as the cocatalyst, Cr is used only in traces in comparison with the amount of Ni or Cu. Accordingly, 0.1 to 0.25 mol of Cr is preferably used per mol of Ni or Cu. When the very particularly preferred combination of Ni or Cu with traces of Cr and Co is used, Co is used in an amount of 0.0001 to 0.003 mol per mol of Ni or Cu.

The process according to the invention is carried out in an organic solvent. Suitable solvents are formic acid, acetic acid, propionic acid and other carboxylic acids or hydroxycarboxylic acids, acetonitrile, propionitrile, benzonitrile and other nitriles, formaldehyde, acetamide, dimethylformamide, dimethylacetamide and other amides, tert-butanol, tert-amyl alcohol and other alcohols, hexane, octane and other aliphatic hydrocarbons, benzene, chloroform, dichloromethane, dichloroethane, carbon tetrachloride, nitrobenzene, nitromethane, ethyl acetate, butyl acetate, dimethyl ether, diethyl ether, diisopropyl ether and mixtures of these solvents. Acetic acid, propionic acid, acetonitrile, benzonitrile, chloroform or dichloromethane are preferably used as solvents. Optionally, the substrate itself may also serve as a solvent, when used in excess. Oxygen in excess, which can be added in the form of pure oxygen or as air, serves as an oxidizing agent. Furthermore, the oxygen can also be diluted with an inert gas, such as, for example, nitrogen, helium, argon or carbon dioxide.

The reaction temperature is dependent on the substrate used and may be between −20 and 100° C.; preferably, the oxidation is carried out at room temperature of from 0 to 30° C. The reaction can be carried out at atmospheric pressure or at superatmospheric pressure.

In the process according to the invention, the substrate to be oxidized is dissolved in one of the above-mentioned solvents and the catalyst system, consisting of the components a) and b), is added. The aldehyde can be added in one portion to the reaction mixture at the beginning of the reaction or metered in over a relatively long period during the reaction. It is also possible initially to introduce a part of the aldehyde at the beginning of the reaction and to meter in the remainder during the reaction.

Depending on the substrate used, the process according to the invention can be used for the preparation of a multiplicity of oxo compounds. Oxo compounds which can be prepared are acids, alcohols, ketones, aldehydes or peroxides. After the end of the reaction, the desired end product can be isolated from the reaction mixture in a simple manner by means of known technologies, such as filtration, precipitation, condensation, distillation, extraction, crystallization, chromatography and the like and, if required, can be purified.

Compared with the prior art, the corresponding oxo compounds are obtained in higher selectivity and yield as well as reaction rate by the process according to the invention.

The $Ni(OAc)_2 \cdot 4H_2O$ used in Examples 1–3 has a purity of 98% (Aldrich) and contains about 100 ppm of Co. The $Ni(OAc)_2 \cdot 4H_2O$ used in Example 4 is 100% pure (Baker).

EXAMPLE 1

0.239 g (1.00 mmol) of $IDB-CONH_2$ was dissolved in 3 ml of acetonitrile. 0.061 g (0.37 mmol) of N-hydroxyphthalimide, 0.0022 g (0.0088 mmol) of nickel acetate and 0.001 g (0.0025 mmol) of chromium(III) nitrate were added. 0.1185 g (1.12 mmol) of benzaldehyde was added in one portion as the cosubstrate. The oxidation was carried out at 1 bar oxygen and room temperature. After a reaction time of 17 hours, the reaction mixture was analyzed by means of HPLC. 36% of oxcarbazepine were obtained with a conversion of 45% (=81% selectivity, based on oxcarbazepine).

EXAMPLE 2

Example 2 was carried out analogously to Example 1. Instead of acetonitrile, acetic acid was used as a solvent. 49% oxcarbazepine were obtained with conversion of 75% (=66% selectivity, based on oxcarbazepine).

EXAMPLE 3

2.38 g (10.0 mmol) of $IDB-CONH_2$ were dissolved in 30 ml of acetic acid. 0.66 g (4.0 mmol) of N-hydroxyphthalimide, 0.0245 g (0.098 mmol) of nickel acetate and 0.0107 g (0.027 mmol) of chromium(III) nitrate were added. 0.3176 g (3 mmol) of benzaldehyde was added in one portion as the cosubstrate. A mixture of 1.096 g (9.2 mmol) of benzaldehyde and 0.1 ml of acetic acid was added in the course of 5 hours. The oxidation was carried out at 1 bar oxygen and room temperature. After a reaction time of 7 hours, the reaction mixture was analyzed by means of HPLC. 53% of oxcarbazepine were obtained with a conversion of 72% (=74% selectivity, based on oxcarbazepine).

Comparative Experiment 1

Analogously to EP 0 824 962, 0.239 g (1.00 mmol) of $IDB-CONH_2$ in acetic acid was oxidized at room temperature and 1 bar oxygen in the presence of 0.057 g (0.35 mmol) of N-hydroxyphthalimide and 0.0063 g (0.0253 mmol) of cobalt acetate as the catalyst system, but without a cosubstrate. 16% of oxcarbazepine were obtained with a conversion of 33% (=48% selectivity).

Comparative Experiment 2

0.245 g (1.03 mmol) of $IDB-CONH_2$ was dissolved in 3 ml of acetonitrile. 0.032 g (0.2 mmol) of N-hydroxyphthalimide was added, but no cocatalyst containing metal salts. A solution of 0.234 g (5.3 mmol) of acetaldehyde in 2.1 g of acetonitrile was added in the course of 180 minutes as the cosubstrate. The oxidation was carried out at 1 bar oxygen and room temperature. After a reaction time of 17 hours, the reaction mixture was analyzed by means of HPLC. 19% of oxcarbazepine were obtained with a conversion of 42% (=45% selectivity, based on oxcarbazepine). This result was poorly reproducible.

EXAMPLE 4

Oxidation of $IDB-CONH_2$ with the addition of different amounts of cobalt.

A mixture of 2.38 g (10 mmol) of $IDB-CONH_2$, 0.66 g (4.0 mmol) of N-hydroxyphthalimide (NHPI), 24.9 mg (0.1 mmol) of $Ni(OAc)_2 \cdot 4H_2O$ and 8.8 mg (25 µmol) $Cr(acac)_3$ was dissolved in $Co(OAc)_2 \cdot 4H_2O$-containing AcOH (31 g of AcOH). A slow stream of oxygen was then blown through the stirred reaction mixture at 22° C. 306 mg (2.9 mmol) of benzaldehyde were added. Thereafter, a mixture of 1.14 g (10.7 mmol) of benzaldehyde and 0.11 g of acetic acid was added in the course of 300 minutes. The reaction mixture was analyzed by means of HPLC after 300 and after 420 minutes. The amount of Co used, the conversion and the yield are shown in Table 1. The time after which the mixture acquired a yellow color is also indicated.

TABLE 1

| Amount of Co (nmol) | Yellow color after x h | Conversion after 5 h | Yield after 5 h | Conversion after 7 h | Yield after 7 h |
|---|---|---|---|---|---|
| 0 | 2 | 50% | 38% | 61% | 43% |
| 20 | 1.5 | 53% | 41% | 65% | 48% |
| 40 | 0.75 | 58% | 44% | 70% | 50% |
| 64 | 0.5 | 61% | 45% | 73% | 50% |
| 82 | 0.5 | 61% | 44% | 73% | 50% |
| 106 | <0.5 | 62% | 41% | 72% | 48% |
| 146 | <0.5 | 65% | 40% | 74% | 46% |
| 210 | <0.3 | 67% | 40% | 75% | 44% |

What is claimed is:

1. In a process for the oxidation of a substrate containing methylene ($CH_2$) groups by means of oxygen oxidation in the presence of a catalyst system consisting of a) an imide compound of the formula

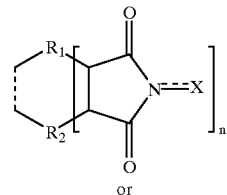

I or

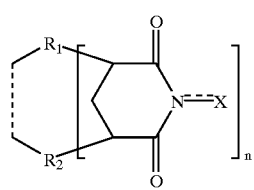

II in which $R_1$ and $R_2$ denote H, OH, halogen, a $C_1$–$C_{20}$-alkyl, alkenyl or alkoxy group, an aryl group, a $C_1$–$C_6$-acyl group, a carboxyl or a $C_1$–$C_{10}$-alkoxycarbonyl group, or $R_1$ and $R_2$ together form a double bond in formula I or form an aromatic or nonaromatic ring system in formula I or II, X denotes O or OH and n is an integer from 1 to 3, and b) a cocatalyst containing one or more elements selected from the group consisting of the transition metals and of the 2A and 3A elements of the Periodic Table, in an organic solvent to give the corresponding oxo compounds, the improvement wherein the substrate is oxidized together with an aromatic or aliphatic aldehyde having 2–20 C atoms.

2. The process as claimed in claim 1, wherein N-hydroxysuccinimide, N-hydroxymaleimide, N-hydroxyhexahydrophthalimide, N,N'-dihydrocyclohexanetetracarboximide, N-hydroxyphthalimide, N-hydroxytetrabromophthalimide, N-hydroxytetrachlorophthalimide, N-hydroxytrimellitimide, N,N'-dihydroxynaphthalenetetracarboximide, N-hydroxy(dodecenyl)succinimide, N-hydroxy(octenyl)succinimide or N-hydroxynaphthalimide is used as component a) of the catalyst system.

3. The process as claimed in claim 1, wherein cocatalysts which contain one or more elements of groups 1B, 4B, 5B, 6B, 7B or 8 of the Periodic Table are used.

4. The process as claimed in claim 3, wherein a cocatalyst which contains a combination of elements of group 6B and 8 or 1B is used.

5. The process as claimed in claim 1, wherein the cocatalyst is used in the form of a formate, acetate, propionate, acetylacetonate, naphthenate, stearate, nitrate, sulfate, phosphate, carbonate or halide.

6. The process as claimed in claim 1, wherein a saturated or unsaturated aliphatic or aromatic aldehyde or dialdehyde having 2–20 C atoms is used as the cosubstrate.

7. The process as claimed in claim 6, wherein acetaldehyde, propionaldehyde, butyraldehyde, valeraldehyde, capronaldehyde, benzaldehyde or o-phthalaldehyde is used as the aldehyde.

8. The process as claimed in claim 1, wherein compounds which contain methylene activated by carboxyl or carbonyl groups are used as a substrate.

9. The process as claimed in claim 1, wherein 0.01 to 0.5 mol of component a), 0.001 mol to 0.3 mol of component b) and 0.1 to 0.3 mol of cosubstrate are used per mol of substrate.

10. The process as claimed in claim 1, wherein formic acid, acetic acid, propionic acid, acetonitrile, propionitrile, benzonitrile, formaldehyde, acetamide, dimethylformamide, dimethylacetamide, tert-butanol, tert-amyl alcohol, hexane, octane, benzene, chloroform, dichloromethane, dichloroethane, carbon tetrachloride, nitrobenzene, nitromethane, ethyl acetate, butyl acetate, dimethyl ether, diethyl ether, diisopropyl ether or mixtures thereof are used as solvents.

* * * * *